United States Patent [19]

Lassalle et al.

[11] Patent Number: 5,476,942
[45] Date of Patent: Dec. 19, 1995

[54] 1-[2-AMINO-5-[1-(TRIPHENYLMETHYL)-1H-IMIDAZOL-4-YL]-1-OXOPENTYL] PIPERIDINE DERIVATIVES, THEIR PREPARATION AND THEIR USE AS SYNTHETIC INTERMEDIATES

[75] Inventors: Gilbert Lassalle, Clamart; Daniel Galtier, Guyancourt; Frédéric Galli, La Celle St Cloud, all of France

[73] Assignee: Synthelabo, Le Plessis Robinson, France

[21] Appl. No.: 305,663

[22] Filed: Sep. 14, 1994

[30]      Foreign Application Priority Data

Sep. 14, 1993 [FR]  France ..................... 93 10906

[51] Int. Cl.$^6$ ................. C07D 401/06; C07D 401/14
[52] U.S. Cl. ........................................ 546/210
[58] Field of Search ............................... 546/210

[56]            References Cited

U.S. PATENT DOCUMENTS 5,098,888  3/1992  Vincent et al. .................. 514/18

OTHER PUBLICATIONS

Nutt et al. "Synthesis of thyrotropin releasing hormone analogues with selective central nervous system effects" J. Med. Chem. v. 24, pp. 692–698 (1981).

*Primary Examiner*—Ceila Chang
*Attorney, Agent, or Firm*—Jacobson, Price, Holman & Stern

[57]              ABSTRACT

Compounds of the formula:

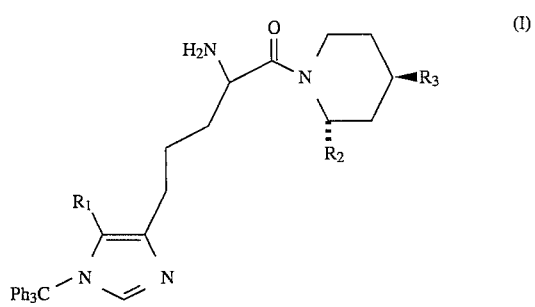

in which $R_1$ represents a hydrogen atom or a $(C_1-C_4)$alkyl group, $R_2$ represents a hydrogen atom, a $(C_1-C_4)$alkoxycarbonyl group, a carboxyl group, a sodium carboxylate group, a group —$CH_2OR_4$, where $R_4$ is a hydrogen atom or $R_4$ is a $(C_1-C_4)$ alkyl or $(C_1-C_4)$ acyl group, a group —$CONR_5R_6$, or a group —$CN_4R_5$, where $R_5$ is a hydrogen atom or a $(C_1-C_4)$alkyl group and $R_6$ is a hydrogen atom or a $(C_1-C_4)$alkyl, hydroxyl or $(C_1-C_4)$ alkoxy or $(C_1-C_3)$ alkoxyphenyl group and $R_3$ represents a $(C_1-C_4)$alkyl group, and their acid addition salts are useful as synthetic intermediates.

5 Claims, No Drawings

1-[ 2-AMINO-5-[ 1-(TRIPHENYLMETHYL)-1H-IMIDAZOL-4-YL] -1-OXOPENTYL] PIPERIDINE DERIVATIVES, THEIR PREPARATION AND THEIR USE AS SYNTHETIC INTERMEDIATES

The present invention provides 1-[ 2-amino-5-[1-(triphenylmethyl)-1H-imidazol-4-yl]-1-oxopentyl] piperidine derivatives, a process for their preparation and their use as synthetic intermediates.

The compounds of the invention correspond to the formula:

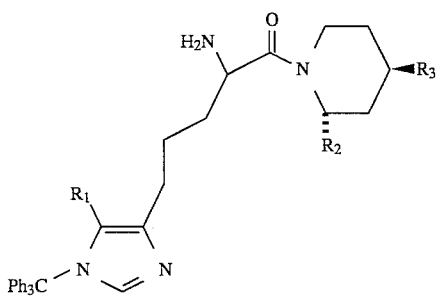
(I)

in which $R_1$ represents a hydrogen atom or a ($C_1$–$C_4$)alkyl group, $R_2$ represents a hydrogen atom, a ($C_1$–$C_4$)alkoxycarbonyl group, a carboxyl group, a sodium carboxylate group, a group —$CH_2OR_4$ (where $R_4$ is a hydrogen atom, a ($C_1$–$C_4$) alkyl or a ($C_1$–$C_4$)acyl group), or group —$CON_5R_6$, or a group —$CN_4R_5$ (where $R_5$ is a hydrogen atom or a ($C_1$–$C_4$)alkyl group and $R_6$ is a hydrogen atom, a ($C_1$–$C_4$)alkyl, a hydroxyl, a ($C_1$–$C_4$)alkoxy or a ($C_1$–$C_3$) alkoxyphenyl group), and $R_3$ represents a ($C_1$–$C_4$)alkyl group.

The preferred compounds according to the invention are those corresponding to the formula (I) in which $R_1$ represents a hydrogen atom or a ($C_1$–$C_4$)alkyl group, $R_2$ represents a carboxyl group, an ethoxycarbonyl group, a hydroxycarboxamide group, a hydroxymethyl group, or a 1H-tetrazolyl group and $R_3$ represents a methyl or ethyl group.

The compounds of the invention possess three asymmetric centres according to the meaning of the substituents.

The preferential configuration of the piperidyl group is [2R,4R].

The preferential configuration of the asymmetric carbon of the central amino acid part

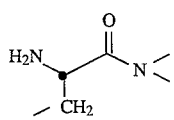

is [S].

The compounds of the invention can exist in the form of free bases or as acid addition salts.

The compounds of formula (I) are useful in the synthesis of compounds possessing antithrombotic activity such as those described in European Patent Application EP 0,565, 396 of the Applicant company.

The compounds according to the invention can be synthesized in the manner shown in the following Diagram 1.

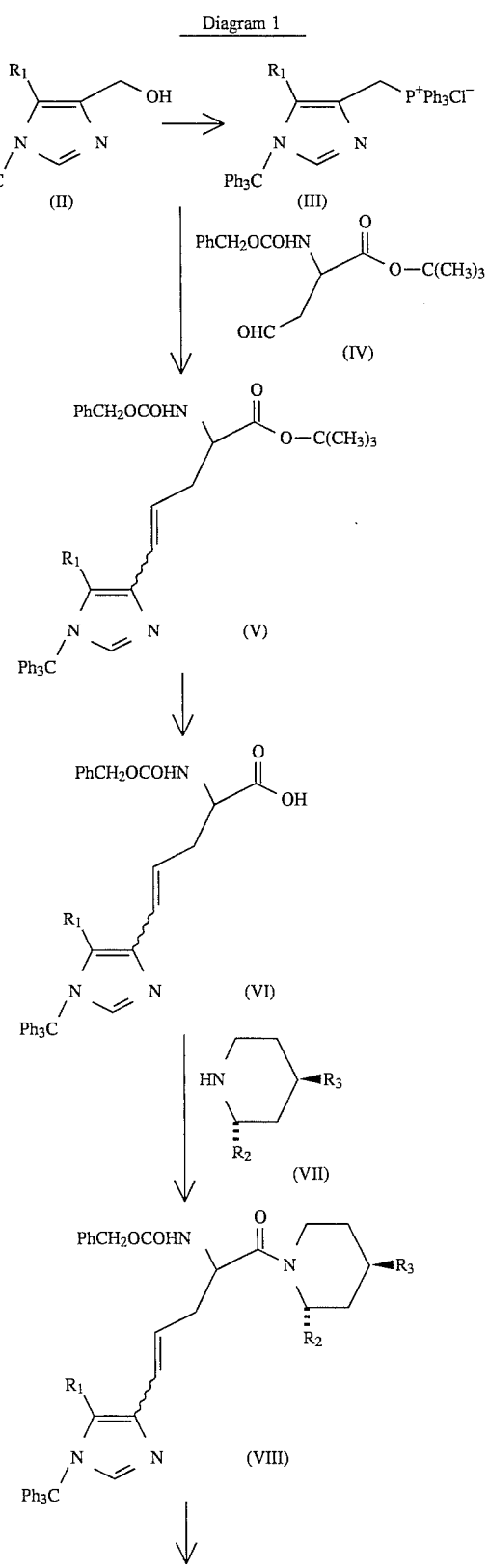

-continued
Diagram 1

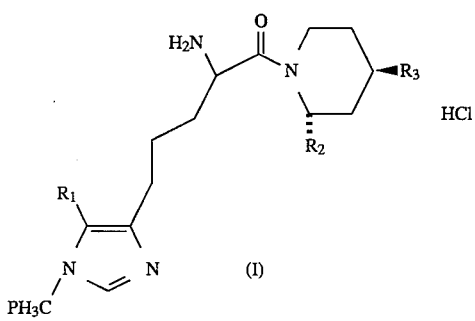

An alcohol of formula (II) is reacted with thionyl chloride in a mixture of dimethylformamide/dichloromethane and the compound obtained is then reacted with triphenylphosphine in a solvent such as dimethylformamide or benzene at a temperature of 80° C. A triphenylmethylphosphonium chloride of formula (III) is obtained which is reacted with a compound of formula (IV). The reaction is carried out in a solvent such as tetrahydrofuran, in the presence of n-butyllithium at a temperature of −70° C. a compound of formula (V) is obtained, in the form of a cis/trans mixture at the double bond. The compound of formula (V) is then reacted with gaseous hydrochloric acid in a solvent such as benzene and a compound of formula (VI) is obtained which is reacted with a compound of formula (VII) in the presence of a base such as N,N-diisopropylethylamine and a coupling agent such as benzotriazol-1-yloxytris(dimethylamino)phosphonium hexafluorophosphate to obtain a compound of formula (VIII). The compound of formula (VIII) is then subjected to a catalytic hydrogenation to obtain a compound of formula (I).

The starting materials are commercially available or described in the literature or can be prepared according to methods which are described therein or which are known to those skilled in the art.

Thus, the compounds of formula (II) can be prepared by methods analogous to those described in European Patent 0,242,973 and to those described by Griffith R. K. et al., Synthesis, 1983, 576. Some compounds of formula (IV) are described by Valerio R. M. et al. in Synthesis, 1988, 786.

The preparation of the piperidines of formula (VII) in which $R_2$ represents a $(C_1-C_4)$alkoxycarbonyl group or a carboxyl group is described in European Patent No. 0,008, 746. The preparation of the other piperidines of formula (VII) is described in European Patent Application EP 0,562, 396 of the Applicant company.

The preparation of the compounds of formula (V) is described in European Patent Application EP 0,562,396 of the Applicant company.

The following Examples illustrate the preparation of some compounds in accordance with the invention. The microanalyses and the IR and NMR spectra confirm the structure of the compounds obtained.

EXAMPLE 1

[2R-[1(2S), 2α,4β]]-1-[2-amino-1-oxo-5-[1-( triphenylmethyl)-1H-imidazol-4-yl]pentyl]-4-methylpiperid-2-yl] methyl acetate hydrochloride.

1.1 triphenyl [[1-(triphenylmethyl)-1H-imidazol-4-yl]methyl]phosphonium chloride 77.7 g (296 mmol) of triphenylphosphine are added to 670 ml of a solution of 105.5 g (294 mmol) of 4-(chloromethyl)-1-(triphenylmethyl)-1H-imidazole in dimethylformamide. The mixture is heated at 80° C. for three hours. The solvent is evaporated and the crude product is taken up in ether and triturated. The precipitate is filtered and dried under vacuum over phosphorus pentoxide.

162 g of product are obtained in the form of yellowish crystals.

Melting point=210° C.; Yield=89%

1.2. 1,1-dimethylethyl (S,E)-2-[[(phenylmethoxy)carbonyl] amino]-5-[ 1-(triphenylmethyl)-1H-imidazol-4-yl]pent-4-enoate 50.93 g (820 mmol) of triphenyl[[1-(triphenylmethyl)-1H-imidazol- 4-yl]methyl]phosphonium chloride in solution in 333 ml of tetrahydrofuran are introduced, under argon, into a three-necked round-bottomed flask. 51.2 ml of a 1.6M solution of n-butyllithium in hexane (820 mmol) are added dropwise, at −70° C. After stirring for 30 minutes at −70° C., the reaction mixture is quickly poured into 270 ml of a 0.253M solution, cooled to −70° C., of 1,1-dimethylethyl (S)-4-oxo-2-[[(phenylmethoxy)carbonyl]amino]butanoate in tetrahydrofuran (683 mmol). The mixture is allowed to return to room temperature overnight. The mixture is hydrolysed with 280 ml of a saturated aqueous sodium chloride solution. The aqueous phase is separated from the organic phase and extracted with 2 times 140 ml of ethyl acetate. The organic phases are combined, dried over magnesium sulphate and evaporated to dryness. Purification is carried out by chromatography on a column of silica gel, the eluent being a hexane/ethyl acetate gradient.

A mixture of cis and trans olefin is obtained. For the cis form:

Melting point=66° C.

$R_f$=0.30 [hexane/ethyl acetate (60/40)] For the trans form:

$R_f$=0.15 [hexane/ethyl acetate (60/40)] Yield=40%

1.3. (S,E)-2-[[(phenylmethoxy)carbonyl]amino]-5-[1-(triphenylmethyl)- 1H-imidazol-4-yl]-4-pentenoic acid 3.9 g (6.37 mmol) of the trans compound obtained in the preceding stage are placed in 80 ml of benzene and then a stream of gaseous hydrochloric acid is passed through at 0° C. until saturation. The mixture is stirred for 4 hours at room temperature and then evaporated to dryness. The residue is taken up in 20 ml of dichloromethane, neutralized with ammonia and purified by chromatography on a column of silica gel, the eluent being a dichloromethane/methanol (90/10) mixture.

3 g of product are obtained. Melting point=180° C. (decomposition)

1.4. Phenylmethyl [2R-[1(1S), 2α, 4β]]-[1-[ [2-(acetyloxy)methyl-4-methylpiperid-1-yl] carbonyl]-4-[1-(triphenylmethyl)-1H-imidazol-4-yl]but-3-enyl]carbamate 1.67 g (3 mmol) of the compound obtained in the preceding stage, 1.5 ml of N,N-diisopropylethylamine and 1.5 g (3.3 mmol) of benzotriazol-1-yloxytris(dimethylamino-)phosphonium hexafluorophosphate are added at 0° C., to a solution of 1.14 g (3 mmol) of (2R-trans)-4-methylpiperid-2-yl)methyl acetate trifluoroacetate (2:1) in 20 ml of dichloromethane. The mixture is left overnight at room temperature and is then poured into 100 ml of ethyl acetate. The solution obtained is washed successively with 100 ml of a 0.1N hydrochloric acid solution, 100 ml of a saturated sodium hydrogencarbonate solution and 100 ml of a saturated sodium chloride solution, dried over magnesium sulphate, and evaporated to dryness. 1.4 g of product are obtained in the form of a solid. Melting point=59° C.

1.5. [2R-[1(2S), 2α, 4β]]-1-[2-amino-1-oxo-5-[ 1-(triphenylmethyl)-1H-imidazol-4-yl] pentyl]-4-methylpiperid-2-yl]methyl acetate hydrochloride 1.3 g (1.8 mmol) of the compound obtained in the preceding stage are placed in a Parr flask and 30 ml of ethanol and 0.4 g of 104 palladium-on-charcoal are added. Hydrogenation is carried out at 50 psi for 8 hours. The mixture is then filtered and the catalyst sucked dry. The filtrate is collected and evaporated to dryness. The residue is taken up in 20 ml of a 0.1N solution of hydrochloric acid in isopropanol and the solution obtained is evaporated to dryness.

1.12 g of product are obtained in the hydrochloride form.

$R_f$=0.55 [methyl isobutyl ketone/acetic acid/water (60/20/20)]

EXAMPLE 2

Ethyl [2R-[1(2S), 2α, 4β]]-1-[2-amino-1-oxo-5-[ 1-(triphenylmethyl)-1H-imidazol-4-yl]pentyl]-4-methylpiperidine-2-oarboxylate hydrochloride 2.1. Ethyl [2R-[1(2S), 2α, 4β]]-4-methyl-1-[ 1-oxo-2-[ [(phenylmethoxy)carbonyl]amino]-5-[ 1-(triphenylmethyl)-1H-imidazol-4-yl]pent-4-enyl]piperidine-2-carboxylate 2.9 g (5 mmol) of the compound obtained according to the method described in Example 1.3, 2.5 ml of N,N-diisopropylethylamine, and then 2.3 g (5.2 mmol) of benzotriazol-1-yloxytris(dimethylamino)phosphonium hexafluorophosphate are added, at 0° C., to a solution of 1.78 g (5 mmol) of ethyl (2R-trans)-4-methylpiperidine-2-carboxylate in 20 ml of dichloromethane. The mixture is left overnight at room temperature and then poured into 100 ml of ethyl acetate. The solution obtained is washed successively with 100 ml of a 0.1N hydrochloric acid solution, 100 ml of a saturated sodium hydrogencarbonate solution and 100 ml of a saturated sodium chloride solution, dried over magnesium sulphate, and evaporated to dryness.

2.4 g of solid product.

Melting point=60°–65° C.

2.2. Ethyl [2R-[1(2S), 2α, 4β]]-1-[2-amino-1-oxo-5-[ 1-(triphenylmethyl)-1H-imidazol-4-yl]pentyl]-4-methylpiperidine-2-carboxylate hydrochloride 1.65 g (2.3 mmol) of the compound obtained in the preceding stage, 30 ml of ethanol and 0.66 g of 10% palladium-on-charcoal are placed in a Parr flask. Hydrogenation is carried out at 50 psi for 4 hours in the cold. The mixture is then filtered and the catalyst sucked dry. The filtrate is collected and evaporated to dryness under reduced pressure. The residue is taken up in 23 ml of a 0.1N solution of hydrochloric acid in isopropanol and the solution obtained is evaporated to dryness.

1.5 g of product are obtained in the hydrochloride form.

Melting point=98° C.

The compounds of the invention are useful in the synthesis of compounds of formula (1)

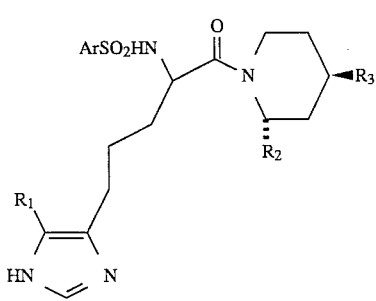

(1)

in which $R_1$, $R_2$ and $R_3$ are as defined above and Ar represents a 1-naphthyl group substituted by a di($C_1$–$C_4$)alkylamino group, a 6,7-di($C_1$–$C_4$)alkoxy-1-naphthyl group, an 8-quinolyl group substituted in the 3-position by a ($C_1$–$C_4$)alkyl group, a 1,2,3,4-tetrahydro-8-quinolyl group substituted in the 3-position by a ($C_1$–$C_4$)alkyl group, or a 1H-indazol-7-yl group.

The synthesis of the compounds of formula (1) from the compounds according to the invention is shown in the following Diagram 2.

Diagram 2

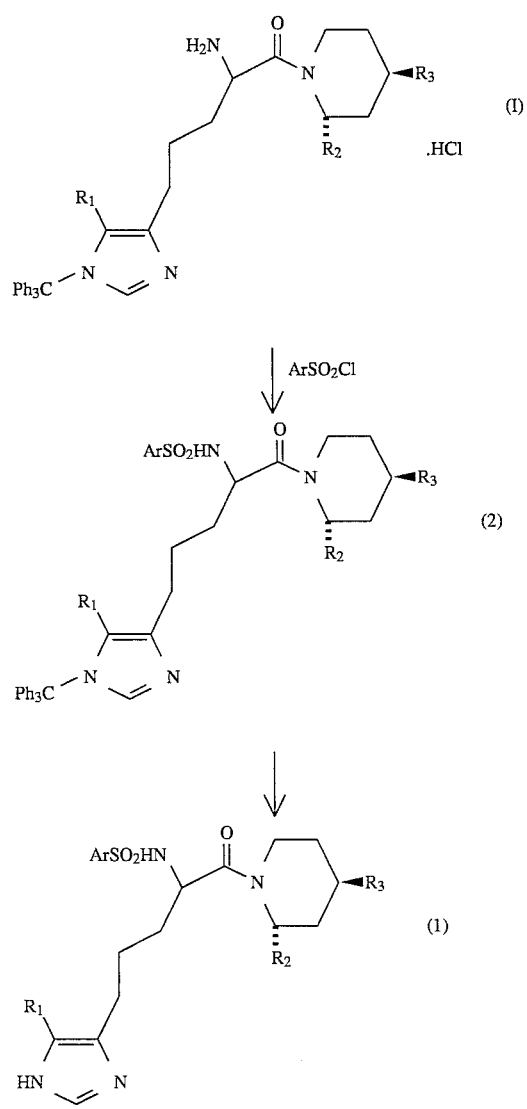

A compound of formula (I) in which $R_1$, $R_2$ and $R_3$ are as defined above is reacted with a compound of formula $ArSO_2Cl$ in which Ar is as defined above and a compound of formula (2) is obtained which is deprotected while hot in the presence of acetic acid.

Example A illustrates this synthesis.

Example A

[2R-[1(2S, 3S), 2α, 4β]]-1-[5-(1H-imidazol-4-yl)-2-[ [(3-methyl-1,2,3,4-tetrahydroquinol-8-yl )sulphonyl]amino]-1-oxopentyl]-4-methylpiperidine-2-methanol A.1. [2R-[1(2S, 3S), 2α, 4β]]-[4-methyl-1-[2-[ [(3-methyl-1,2,3,4-tetrahydroquinol-8-yl) sulphonyl]amino]-1-oxo-5-[1-(triphenylmethyl)-1H-imidazol-4-yl] pentyl]piperid-2-yl]methyl acetate A.1.1. (S)-3-methyl-1,2,3,4-tetrahydroquinoline-8-sulphonic acid chloride A.1.1.1. Methyl (S)-α-methyl-2-nitrobenzenepropanoate 9.5 g (42 mmol) of methyl (R)-3-iodo-2-methylpropanoate are placed, under a nitrogen atmosphere and with stirring, in 90 ml of benzene containing 4.4 g of Zn(Cu) couple and 5.5 ml of dimethylacetamide. The mixture is stirred for 15 minutes at room temperature and then heated at 60° C. for 3 hours. The mixture-is allowed to cool to room temperature and 1 g of bis(tri-O-tolylphosphine)palladium acetate in suspension in 2 ml of benzene followed by 7.5 g (30 mmol) of 1-iodo-2-nitrobenzene in solution in 20 ml of benzene are added. The mixture is heated at 60° C. for 1 hour, 100 ml of ethyl acetate are added and the reaction mixture is then filtered through celite. The filtrate is washed with 100 ml of a 1N hydrochloric acid solution and then with 100 ml of water, dried over magnesium sulphate and evaporated to dryness. The residue is purified by chromatography on a column of silica gel, the eluent being a hexane/ethyl acetate (90/10) mixture. 3 g of product are obtained in the form of an oil which is used as it is in the following stage.

A.1.1.2. (S)-3-methyl-3,4-dihydroquinol-2(1H)-one

Method 1

3 g (14 mmol) of the product obtained in the preceding stage are placed in 40 ml of methanol and 100 mg of platinum oxide are added. Hydrogenation is carried out under a pressure of 50 psi in a Parr apparatus for 8 hours. The mixture is then filtered, the catalyst is sucked dry, and the filtrate is evaporated to dryness. The residue is recovered and triturated in ether. It is recrystallized from ethyl ether.

1.5 g of product are obtained in the form of crystals.

Melting point=117°–119° C.

Method 2

31 g (135 mmol) of methyl (R)-3-iodo-2-methylpropanoate are placed, under a nitrogen atmosphere and with stirring, in 310 ml of benzene containing 19.75 g of Zn(Cu) couple and 20.3 ml of dimethylacetamide. The mixture is heated at 60° C. for 3 hours and is then cooled to room temperature. 2.92 g of bis(tri-O-tolylphosphine)palladium acetate are added in a single step, and then 19.75 g (90 mmol) of 2-iodoaniline in solution in 50 ml of benzene are added. The mixture is heated for 1 hour at 50° C. and then allowed to cool to room temperature. The mixture is then filtered through celite, and washed with 2 times 100 ml of ethyl acetate. The filtrates are collected, washed successively with 2 times 100 ml of a 1N hydrochloric acid solution, 100 ml of a saturated sodium hydrogencarbonate solution, and 50 ml of a saturated sodium chloride solution, dried over magnesium sulphate, and evaporated to dryness. The residue is purified by chromatography on a column of silica gel, the eluent being dichloromethane. 4.9 g of product are obtained.

Melting point=118°–120° C.

A.1.1.3. (S)-3-methyl-1,2,3,4-tetrahydroquinoline 0.8 g (5 mmol) of the compound obtained in the preceding stage is placed in 6 ml of tetrahydrofuran and 17.5 ml of a 1M solution of borane in tetrahydrofuran are added at 0° C. under a nitrogen atmosphere. The mixture is heated at reflux for 1 hour and 5 ml of water are slowly added. The pH of the reaction mixture is then adjusted to 1 with a 1N hydrochloric acid solution and heating is then carried out at reflux for 2 hours. The mixture is allowed to cool and is evaporated. The residue is taken up in 50 ml of ethyl acetate and the solution obtained is washed with 2 times 50 ml of sodium hydrogencarbonate solution, dried over magnesium sulphate, and evaporated to dryness. The residue thus obtained is purified by chromatography on a column of silica gel, the eluent being dichloromethane.

0.6 g of product is obtained in the form of an oil which is used as it is in the following stage. $[\alpha]_D=+79°$ (c=3, methanol)

A.1.1.4. (S)-5-methyl-5,6-dihydro-2H, 4H-thiazolo[5,4,3-ij]quinol-2-one 40.5 ml of toluene and 2.28 ml (27 mmol) of chlorocarbonylsulphenyl chloride are placed under a nitrogen atmosphere and stirred and cooled to −50° C. A mixture of 3.5 g (23 mmol) of the compound obtained in the preceding stage and 3.24 g (28 mmol) of N,N-dimethylbenzeneamine in solution in 130 ml of toluene is then slowly added. The mixture is allowed to return to room temperature, 100 ml of toluene are added, and the mixture is heated at 80° C. for 3 hours. The mixture is allowed to cool and is then washed with 2 times 100 ml of a 1N hydrochloric acid solution and with 100 ml of a saturated NaCl solution, dried over magnesium sulphate, and evaporated to dryness. The residue thus obtained is purified by chromatography on a column of silica gel, the eluent being dichloromethane. 4.3 g of product are obtained.

Melting point=54°–56° C.

A.1.1.5. (S) -8,8'-dithiobis (3-methyl-1,2,3,4-tetrahydroquinoline)

1.4 g (6.8 mmol) of the compound obtained in the preceding stage are taken up in 14 ml of 3N alcoholic potassium hydroxide and heated at reflux for 6 hours. The reaction mixture is poured into 50 ml of water and the pH of the mixture is adjusted to 4–5 with hydrochloric acid. The mixture is extracted with ether, and the ether phase is collected, dried over magnesium sulphate and evaporated to dryness. The residue is taken up in 50 ml of benzene and 10 g of alumina are added. The mixture is stirred while exposed to the air for 18 hours. The alumina is filtered off and washed with dichloromethane. The filtrates are combined and evaporated to dryness. The residue is purified by chromatography on a column of silica gel, the eluent being a cyclohexane/ethyl acetate (95/5) mixture. 0.8 g of yellow product is obtained.

Melting point=78°–80° C.

A.1.1.6. (S)-3-methyl-1,2,3,4-tetrahydroquinoline-8-sulphonic acid 0.8 g (4.5 mmol) of the compound obtained in the preceding stage is dissolved in 4.51 g of a 95 % sulphuric acid solution. The reaction mixture is placed in an ice bath and 1.49 ml of 35 % hydrogen peroxide are slowly added. Water and then ice are added to the reaction mixture and the precipitate obtained is filtered off, washed successively with 5 ml of ice-cold water, 3 times 20 ml of ether and 10 ml of ice-cold methanol, and finally rinsed with ether and dried in an oven under reduced pressure. 0.5 g of product is obtained.

Melting point=255° C. (decomposition) $[\alpha]_D=+38°$ [c=0.2, methanol/water (50/50)]

A.1.1.7. (S)-3-methyl-1,2,3,4-tetrahydroquinoline-8-sulphonic acid chloride 1.07 g of triphenylphosphine are dissolved in 7.5 ml of dichloromethane at 0° C. 0.3 ml of sulphuryl chloride is added dropwise under a nitrogen atmosphere at 0° C. and the mixture is then allowed to return to room temperature. A solution containing 0.47 g (2.1 mmol) of the acid obtained in the preceding stage, 0.3 ml of triethylamine and 12 ml of dichloromethane is then slowly added. The mixture is stirred for 1 hour at room temperature, poured into 200 ml of pentane, and filtered. The filtrate is evaporated to dryness and the residue is taken up in 100 ml of pentane and the solution obtained is evaporated to dryness. 0.4 g of product is obtained which is used as it is in the following stage.

A.1.2. [2R-[1(2S, 3S), 2α, 4β]]-[4-methyl-1-[2-[[ (3-methyl-1,2,3,4-tetrahydroquinol-8-yl) sulphonyl]amino]-1-oxo-5-[1-(triphenylmethyl)-1H-imidazol-4-yl] pentyl]piperid-2-yl]methyl acetate 0.4 g (2 mmol) of (S)-3-methyl-1,2,3,4-tetrahydroquinoline-8-sulphonic acid chloride obtained according to the method described above in solution in 10 ml of dichloromethane and 0.38 ml of triethylamine in 10 ml of dichloromethane are added, at 0° C., to 0.6 g (0.9 mmol) of the compound obtained in Example 1. The mixture is left stirring overnight at room temperature and then washed successively with 10 ml of a 0.2N hydrochloric acid solution, 10 ml of a saturated sodium hydrogencarbonate solution and 10 ml of a saturated sodium chloride solution. The solution obtained is filtered, dried over magnesium sulphate and evaporated to dryness. The residue is purified by chromatography on a column of silica gel, the eluent being a dichloromethane/ethanol (96/4) mixture. 0.96 g of product is obtained.

Melting point=49° C.

A.2. [2R-[1(2S, 3S), 2α, 4β]]-[1-[ 5-(1H-imidazol-4-yl)-2-[[(3-methyl-1,2,3,4-tetrahydroquinol-8-yl) sulphonyl] amino]-1-oxopentyl]-4-methylpiperid-2-yl]methyl acetate 0.65 g (0.74 mmol) of the compound obtained in the preceding stage is placed in 10 ml of acetic acid. 2 ml of water and 8 ml of tetrahydrofuran are added and the mixture is then heated at 80° C. for 1 hour. The reaction mixture is evaporated to dryness and the residue is purified by chromatography on a column of silica gel, the eluent being a dichloromethane/ethanol (90/10) mixture.

0.4 g of pure product is obtained.

Melting point=47° C.

A.3. [2R-[1(2S, 3S), 2α, 4β]]-1-[5-( 1H-imidazol-4-yl)-2-[ [(3-methyl-1,2,3,4-tetrahydroquinol-8-yl )sulphonyl] amino]-1-oxopentyl]-4-methylpiperidine-2-methanol 0.4 g (0.75 mmol) of the compound obtained in the preceding stage is placed in 2 ml of methanol, and cooled to 0° C., and 1.5 ml of a 1N sodium hydroxide solution are added dropwise. The mixture is left stirred for 2 hours at 0° C., the methanol is evaporated, and the residue is suspended in a dichloromethane/water (50/50) mixture. The organic phase is recovered, dried over magnesium sulphate and evaporated to dryness. The residue is taken up in a 1N hydrochloric acid solution and is purified by chromatography on a column of silica gel, the eluent being a 0.01N hydrochloric acid and acetonitrile gradient (0 to 100% acetonitrile). The fractions containing the product are combined and lyophilized.

0.3 g of product is obtained.

Melting point:=90° C.

$[\alpha]_D$=+110° (c=0.2, methanol)

The compounds of formula (1) thus obtained have antithrombotic properties and are described in European Patent Application EP 0,565,396 of the Applicant company.

We claim:

1. A compound of the formula:

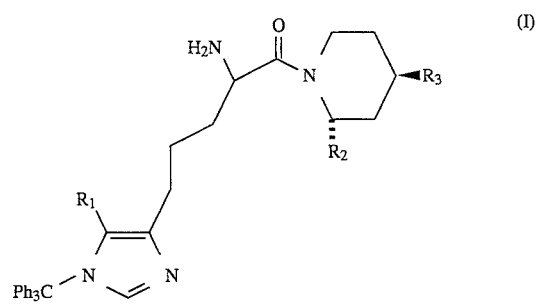

in which $R_1$ represents a hydrogen atom or a $(C_1-C_4)$alkyl group, $R_2$ represents a hydrogen atom, a $(C_1-C_4)$alkoxycarbonyl group, or a carboxyl group, a sodium carboxylate group, a group —$CH_2OR_4$ (where $R_4$ is a hydrogen atom, a $(C_1-C_4)$alkyl or a $(C_1-C_4)$acyl group), a group —$CON_5R_6$, or a tetrazolyl group optionally substituted with a $(C_1-C_4)$alkyl group, (where $R_5$ is a hydrogen atom or a $(C_1-C_4)$ alkyl group and $R_6$ is a hydrogen atom, a $(C_1-C_4)$ alkyl, a hydroxyl, a $(C_1-C_4)$alkoxy or a $(C_1-C_3)$ alkoxyphenyl group), and $R_3$ represents a $(C_1-C_4)$ alkyl group, and its acid addition salts.

2. a compound according to claim 1, wherein $R_1$ represents a hydrogen atom or a $(C_1-C_4)$alkyl group, $R_2$ represents a carboxyl group, an ethoxycarbonyl group, a hydroxycarboxamide group, a hydroxymethyl group, or a 1 H-tetrazolyl group, and $R_3$ represents a methyl or ethyl group.

3. A compound according to claim 1, wherein the piperidyl group has the configuration and the asymmetric carbon of the central amino acid part:

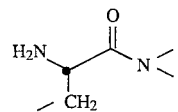

has the configuration.

4. A compound according to claim 1 which is [2R-[1(2 S), 2α,4β]]-[1-[2-amino-1-oxo-5-[ 1-(triphenylmethyl)-1 H-imidazol-4-yl]pentyl]-4-methylpiperid- 2-yl]methyl acetate or an acid addition salt thereof.

5. A compound according to claim 1 which is ethyl [2 R-[1(2S), 2α, 4β]]-1-[2-amino-1-oxo-5-[ 1-(triphenylmethyl)-1 H-imidazol-4-yl]pentyl]-4-methylpiperidine-2-carboxylate or an acid addition salt thereof.

* * * * *